US005670540A

United States Patent [19]
Horrobin et al.

[11] Patent Number: 5,670,540
[45] Date of Patent: Sep. 23, 1997

[54] TRIGLYCERIDES OF FATTY ACIDS

[75] Inventors: David F. Horrobin, Guildford; Philip Knowles, Carlisle; Mehar Singh Manku, Carlisle; Austin McMordie, Carlisle, all of England

[73] Assignee: Scotia Holdings PLC, United Kingdom

[21] Appl. No.: 440,987

[22] Filed: May 15, 1995

Related U.S. Application Data

[63] Continuation of Ser. No. 187,044, Jan. 27, 1994, abandoned.

[30] Foreign Application Priority Data

Jan. 27, 1993 [GB] United Kingdom ............... 9301582
Jan. 29, 1993 [GB] United Kingdom ............... 9301801

[51] Int. Cl.$^6$ ............................................ A61K 31/22
[52] U.S. Cl. ............................................ 514/549
[58] Field of Search ........................... 514/549, 551, 514/560

[56] References Cited

U.S. PATENT DOCUMENTS

| | | | |
|---|---|---|---|
| 4,328,243 | 5/1982 | Horrobin | 514/560 |
| 4,528,197 | 7/1985 | Blackburn | 514/552 |
| 4,847,296 | 7/1989 | Babayan et al. | 514/552 |
| 5,059,622 | 10/1991 | Sears | 514/549 |
| 5,231,085 | 7/1993 | Alexander et al. | 514/44 |
| 5,246,726 | 9/1993 | Horrobin | 424/646 |

FOREIGN PATENT DOCUMENTS

| | | |
|---|---|---|
| 0 271 909 | 6/1988 | European Pat. Off. . |
| 0 300 844 | 1/1989 | European Pat. Off. . |
| 0 520 624 A1 | 12/1992 | European Pat. Off. . |
| 0 517 425 | 12/1992 | European Pat. Off. . |
| 2 181 349 | 4/1987 | United Kingdom . |
| WO 94/10125 | 5/1994 | WIPO . |

OTHER PUBLICATIONS

Higashida; STN International, Karlsrueh file 'CA', Chemical Abstracts. AN=CA112(23):215269m (1990).
Xiao; STN International, Karlsruhe File 'CA', Chemical Abstracts. AN=CA106(8):55597n (1986).
Terumo Corp.; Database WPI; Derwent Publications Ltd., AN 85-319801 [51](1985).
Chisso Corp.; Patent Abstracts of Japan; vol. 13, No. 190 (C-593) (1987).
Hartop; BR. .Dermatol., vol. 95, No. 3, 1976; pp. 255–264.
Nair; J. Nat. Prod., vol. 51, No. 1, 1988; p. 184.
Nakamura; Clin. Sci., vol. 84, No. 5, May 1993; pp. 511–516.
J. High Resolut Chromatogr.vol. 25, No. 4, 1992 Aitzetmuller "Separation of highly . . . ".

*Primary Examiner*—Raymond Henley, III
*Attorney, Agent, or Firm*—Nixon & Vanderhye

[57] ABSTRACT

A triglyceride for use in therapy or as a nutritional supplement, or a composition containing a triglyceride, wherein the triglyceride comprises a fatty acid selected from gamma-linolenic acid and the n-6 EFAs naturally derived therefrom and stearidonic acid and the n-3 EFAs naturally derived therefrom, forming a triple ester with glycerol or alternatively forming a double ester in which the other esterifying acide is a single residue of linoleic acid, with the proviso that the di-gammalinolenoyl-mono-linoleoyl glyceride if selected is used as a preparation containing more than 20% by weight thereof.

14 Claims, No Drawings

TRIGLYCERIDES OF FATTY ACIDS

This is a Continuation of application Ser. No. 08/187,044, filed Jan. 27, 1994, now abandoned.

FIELD OF INVENTION

The invention relates to triglycerides.

BACKGROUND

The essential fatty acids (EFAs) consist of a series of twelve compounds illustrated in Table 1 below. Although linoleic acid the parent compound of the n-6 series of EFAs, and alpha-linolenic acid the parent compound of the n-3 series, are usually the main dietary EFAs, these substances as such have relatively minor roles in the body. In order to be fully useful to the body, the parent compounds must be metabolized by the sequence of reactions shown in Table 1. In quantitative terms, as judged by their levels in cell membranes and in other lipid fractions, dihomo-gamma-linolenic acid (DGLA) and arachidonic acid (AA) are the main EFA metabolites of the n-6 series, while eicosapentaenoic acid (EPA) and docosahexaenoic acid (DHA) are the main metabolites of the n-3 series. DGLA, AA, EPA and DHA are important constituents of most of the lipids in the body. As well as being important in themselves they can also give rise to a wide range of oxygenated derivatives, the eicosanoids, including the prostaglandins, leukotrienes and other compounds.

The elongation reactions shown in Table 1, in which 2 carbon atoms are added to the chain, tend to be rapid, whereas the desaturation reactions in which an extra double bond is introduced tend to be very slow. Thus for example gamma-linolenic acid (GLA) is rapidly converted to DGLA while stearidonic acid is readily converted to 20:4n-3 and so these pairs of compounds are equivalent in dietary terms. However, DGLA is only slowly converted to AA. None of the reactions are normally reversible, in man, nor are n-3 and n-6 series acids inter-convertible.

TABLE 1

| n-6 | | n-3 |
|---|---|---|
| 18:2 delta-9,12 (linoleic acid) | ↓ delta-6 desaturase | 18:3 delta-9,12,15 (alpha-linolenic acid) |
| 18:3 delta-6,9,12 (gamma-linolenic acid) | ↓ elongation | 18:4 delta-6,9,12,15 (stearidonic acid) |
| 20:3 delta-8,11,14 (dihomo-gamma-linolenic acid) | ↓ delta-5 desaturase | 20:4 delta-8,11,14,17 |
| 20:4 delta-5,8,11,14 (arachidonic acid) | ↓ elongation | 20:5 delta-5,8,11,14,17 ('eicosapentaenoic acid') |
| 22:4 delta-7,10,13,16 (adrenic acid) | ↓ delta-4 desaturase | 22:5 delta-7,10,13,16,19 |
| 22:5 delta-4,7,10,13,16 | ↓ | 22:6 delta-4,7,10,13,16,19 ('docosahexaenoic acid') |

The acids, which in nature are of the all-cis configuration, are systematically named as derivatives of the corresponding octadecanoic, eicosanoic or docosanoic acids, e.g. delta-9, 12-octadecadienoic acid or delta-4,7,10,13,16, 19-docosahexaenoic acid, but numerical designations such as, correspondingly, 18:2 n-6 or 22:6 n-3 are convenient. Initials, for example, EPA for the 20:5 n-3 acid (eicosapentaenoic acid) or DHA for the 22:6 n-3 acid (docosahexaenoic acid), are also used but do not serve when n-3 and n-6 acids of the same chain length and degree of unsaturation exist as for example with the 22:5 acids. Trivial names in more or less common use in the n-6 series are as shown. Of the n-3 series only 18:3 n-3 has a commonly used trivial name, alpha-linolenic acid, though the name stearidonic acid is coming into use for the 18:4 n-3 acid and the names eicosapentaenoic acid and docosahexanenoic acid as such are also used.

Therapeutic Effects

It is becoming apparent that in many different disease states there are abnormalities of EFA biochemistry leading to abnormal EFA levels in various lipid fractions and in various tissues. These diseases include diseases of the heart and circulation such as hypertension and coronary and peripheral vascular disease, diseases of inflammation and immunity such as atopic disorders, osteoarthritis, rheumatoid arthritis, ulcerative colitis, Crohn's disease and various disorders going under the general classifications of inflammatory or auto-immune, neurological disorders such as Alzheimer's disease, Parkinson's disease and multiple sclerosis, disorders of the kidney, disorders of the skin, disorders of the gastrointestinal tract, disorders of metabolism of calcium and other minerals, disorders of bone and connective tissue, disorders of the reproductive and endocrine systems, psychiatric disorders including schizophrenia and dementias, and disorders of aging.

In particular gamma-linolenic acid (GLA) and dihomogamma-linolenic acid (DGLA) have been claimed to have many therapeutic effects in a wide variety of conditions including, particularly, skin disorders, disorders of inflammation and immunity, cardiovascular disorders and cancer. Forms of GLA proposed include glycerides, salts, free acids and phospholipids.

It used to be thought sufficient, both in nutrition and in therapy of disease, to supply linoleic and alpha-linolenic acids, when the body's own metabolism would invariably do the rest. It has now been evident for some time that this is not true. Different diseases have different abnormal patterns of EFAs and because of problems in metabolism these cannot be corrected simply by giving linoleic acid or alpha-linolenic acid. Many examples of this type of situation are given in papers by the inventor Horrobin D. F. Rev. Contemporary Pharmacotherapy 1990: 1:1–41, Horrobin D. F. Progress Lipid Res 1992: 31: 163–194 and Horrobin D. F. and Manku M. S. pp. 21–53 in "Omega-6 Essential Fatty Acids" Ed. Horrobin, D. F. New York: Wiley-Liss, 1990.

It is therefore appropriate in some situations to give particular EFAs. The usual way to do this is to give natural oils that predominate in or at least contain significant amounts of the particular EFA. For example, GLA is usually isolated in the form of natural oils from plants or fungi and as far as we are aware no-one has ever used tri-GLA as a pharmaceutical or dietary supplement. However there is evidence that in some instances the other EFAs in such oils interfere with the absorption, transport or use of the particular EFA.

The Invention

We have developed methods of purifying GLA and of using the pure GLA to make tri-GLA which is from 90% to 99.9% pure. We have also prepared pure DGLA by chemically adding two carbon atoms to GLA and have been able to make tri-DGLA in purities ranging from 90% to 99.9%. Broadening from this, we propose the use in therapy or as a dietary supplement of the ten "6-desaturated" EFAs of Table 1 (i.e. those arising by or subsequent to the action of the 6-desaturase), as their triglycerides, in particular for example tri-(gammalinolenoyl)-glycerol and tri-(dihomogammalinolenoyl)-glycerol, or alternatively as the corresponding triglycerides containing one linoleoyl residue and two residues of the respective 6-desaturated EFA.

Especially, we propose pharmaceutical compositions containing oils which are at least 60%, preferably 80% and desirably 95% or more pure tri-GLA or other triglyceride as above. Oils may be used for oral, topical, enteral, parenteral or any other route of administration. Certainly a specified particular triglyceride desirably forms more than 10%, preferably more than 30%, very preferably more than 70% and ideally more than 90% of the triglycefide present in any triglyceride material used for the preparation of pharmaceutical compositions, foods, or skin care products. The triglycerides may be made up into appropriate pharmaceuticals or foods so as to provide a dose of ling to 100 g per day, preferably 10 mg to 10 g and very preferably 500 mg to 4 g. Alternatively in foods or skin care products the triglycerides may be incorporated in concentrations or 0.001 to 50%, preferably 0.05 to 20% and very preferably 0.1 to 5%.

The EFAs are exceptionally susceptible to oxidation and so it may be appropriate to co-administer the above triglycerides with oleic acid, which has potent properties as an antioxidant, for example as such or in the form of its triglyceride.

Experimental Work

The background to the use of triglycerides with a linoleoyl group is as follows:

Tri-GLA, tri-DGLA and the other single fatty acid triglycerides may be unusually stable to digestion and therefore not optimally bioavailable. This possibility emerged when we were investigating the digestibility of different triglycerides in vitro using pancreatic lipase. The splitting of free fatty acids from triglycerides to give diglycerides and monoglycerides is regarded as a critical step in the digestion of triglycerides.

We compared the rate of digestion of tri-linoleic acid and tri-GLA in the presence of an appropriate amount of pancreatic lipase for a period of 5 minutes. At the end of five minutes the reaction was stopped and the amount of undigested triglyceride assayed. With tri-LA at the end of five minutes, 27% of the triglyceride had been broken down but with tri-GLA in the same period more than 95% of the material remained in the form of unchanged tri-GLA. This could have a negative impact on digestion and on the bioavailability of the product.

We therefore tested the possibility that the triglyceride might be more easily digested if one linoleic acid molecule were to replace one of the GLAs in tri-GLA. This might possibly allow the enzyme to obtain better access to the triglyceride. We therefore synthesised tri-GLA using 14-C labelled GLA, and a triglyceride with two GLA molecules and one LA molecule, the GLA being labelled with C-14. We exposed the two triglycerides to pancreatic lipase for five minutes, isolated the remaining triglyceride and estimated the amount of radioactivity released. At the end of five minutes, in the case of tri-GLA just over 95% of the radioactivity remained in the tri-GLA form, whereas in the case of di-GLA-mono-LA, only 88% of the radioactivity remained in the triglyceride form. Thus the rate of digestion of the compound containing one LA was more than twice as great as the pure tri-GLA. Di-GLA-mono-LA, while not as easily digestible as tri-LA, was more easily digestible than tri-GLA. The present invention thus comprehends triglycerides containing one linoleic acid and two molecules of a fatty acid which has undergone 6-desaturation as a way of delivering those fatty acids in a relatively digestible form.

Sources, Synthesis

Di-GLA-mono-LA (LGG) is a triglyceride found in substantial amounts in borage oil. The amounts vary depending on the source of the oil but are usually less than 10%. No special attention has ever been paid to LGG and there is nothing specific in any literature about its biological properties. As far as we are aware it is not found in any known preparation at a concentration higher than 20%. Preparations of such concentrations are therefore an aspect of the invention. Also as far as we are aware the other triglycerides described in this application are not found in nature at all. The ones of particular interest are triglycerides in which one fatty acid consists of linoleic acid and the other two are either GLA as above or the completely new compounds with DGLA, arachidonic acid, EPA or DHA.

These triglycerides may be prepared in several different ways by those skilled in the art. One approach is to purify the individual fatty acids and then to mix them in a ratio of two parts of the specific fatty acid with one of LA in a reaction vessel. The triglycerides may then be synthesised by a chemical reaction using, for example, zinc as a catalyst, or by the use of appropriate enzymes. The resulting mix of triglycerides can be used as such or, if appropriate, can be further purified by using techniques such as low temperature crystallisation, selective solvent extraction or the various forms of chromatography including high pressure liquid chromatography, to produce a mixture of TGs in which LGG predominates but in which there are smaller amounts of LLG, LLL and GGG. This mixture can be used itself or further purified. Similar techniques can be used for any of the triglycerides.

Broadly, the triglycerides may preferably be prepared as follows:

a) The individual fatty acids are purified from natural animal, vegetable or microbial sources or are chemically synthesized by methods known in themselves to those skilled in the art or by methods to be developed in the future. For example, particular fatty acids may be separated by such techniques as low temperature crystallisation, urea complex formation, silver complex formation, differential solubility and various forms of chromatography including high pressure liquid chromatography.

b) The individual fatty acids are then esterified with glycerol by chemical or enzymatic methods known in themselves to those skilled in the art or to be developed in the future. For example, the fatty acids and glycerol may be allowed to react together in the presence of one of a number of appropriate enzymes, or of p-toluene sulphonic acid hydrate.

c) If required, through the presence of undesired acids in the starting individual fatty acid, the specific triglycerides are further purified by appropriate methods known to those skilled in the art, in particular high pressure liquid chromatography or other appropriate forms of chromatography; low temperature crystallisation; or the use of solvents which differentially select triglycerides of particular composition.

EXAMPLES OF PREPARATION

Example 1

Preparation of Tri-(z,z,z octadec-6,9,12-trienoyl) glycerol (Tri-all cis GLA, Tri-GLA)

An example of the manufacture of tri-GLA is as follows:

1. Borage oil as a GLA-rich natural oil is saponified/hydrolysed to obtain the free fatty acids, GLA 8–25%.

2. The GLA is concentrated by two stages of urea crystallisation or low-temperature crystallisation to 45–50% GLA initally then to a product in which 70 to 95% of the material is GLA, reducing or eliminating the saturated, monounsaturated and diunsaturated fatty acids.

3. The fatty acid concentrate is distilled using short path distillation under vacuum to remove all the non fatty acid material present (170° C./vacuum $10^{-2}$ mB).

4. Reverse phase HPLC is used to purify the GLA and collect the pure GLA fractions. The fatty acid mixture from stage 3 is dissolved in a mobile phase at 20% by weight. Appropriate mobile phases are mixtures of $CH_3OH$ and water or $CH_3CN$ and water. The stationary phase can be a monophasic C-18 reverse phase silica packing material. Detection is by a refractive index detector or by a UV detector reading at 210 or 215 nM. A suitable HPLC system is a CEDI 1000 system fitted with two 10cm diameter cartridges. The GLA peak emerging from the HPLC system is collected.

5. Residual solvent is removed under vacuum and mild heat and any residual water by redissolving the product in a small volume of hexane and passing through anhydrous sodium sulphate. The final product is obtained by evaporation of the hexane, GLA 99% +.

6. Finally pure GLA from (5) is stirred and heated under vacuum to 140° C. with a small stream of nitrogen passing through the liquid. To each 100 g of GLA is added a solution of p-toluene sulphonic acid in warm glycerol (1.8 g in 10.2 g) over a period of 10 min. The mixture is then kept under these conditions for 6 hours, the water formed in the reaction being condensed out in an ice-cooled vessel. After cooling, the reaction mixture is purified by MPLC using a 500 mm×65mm diameter column packed with Matrex silica, pore size 60A, particle size 35–70 μm. The solvent used is initally hexane, then 5% diethyl ether in hexane. The solvent is finally removed by distillation under vacuum to give tri-GLA as a pale yellow oil, 99.5%.

Other pure single fatty acid triglycerides may be made in a corresponding way.

Example 2

Preparation of di-(z,z,z octadec-6,9,12-trienoyl)-mono-(z,z octadec-9,12-dienoyl) glycerol (LGG)

By the method of the above example pure GLA is prepared, and correspondingly pure linoleic acid.

A 2:1 molar mixture of the free acids is then prepared and reacted with glycerol by the method of stage 6 of that example.

Finally preparative MPLC (medium pressure liquid chromatography) is applied to the mixture of LGG, LLG, LLL and GGG, again as in the example of preparation of GGG, to give the title compound as a clear oil, purity >99.5%.

The same method may be applied in the preparation of other glycerides with one residue of linoleic acid and two residues of a "6-desaturated" fatty acid other than gamma-linolenic acid. Equally for LGG itself the triglycerides of borage oil may be purified by fractionation followed by the application of MPLC to give the essentially pure material.

Example 3

Preparation of Tri-(z,z,z eicosa-8,11,14-trienoyl) glycerol (Tri-DGLA)

First, DGLA is prepared chemically from GLA as follows:

Stage 1: z,z,z octadeca-6,9,12-trienyl methylsulphonate:- To a solution of z,z,z octadeca-6,9,12-trienol (175.5 g) and dry pyridine (83 ml) in dichloromethane (900 ml) cooled to 0°–5° C. and under nitrogen was added methylsulphonyl chloride (121.6 g) over a period of 30 minutes. The mixture was stirred for 48 hours at room temperature diluted with diethyl ether (4000 ml) and the organic layer washed with 2M hydrochloric acid (400 ml) and finally with brine (3×1000 ml). After drying ($MgSO_4$), the solvents were removed in vacuo (50° C./20 mmHg and 25° C./0.01 mmHg) to give crude z,z,z octadeca-6,9,12-trienyl methylsulphonate (226 g,99%) as a dark oil. This crude material was used for the next stage.

Stage 2: 2-(z,z,z octadeca-6,9,12-trienyl) propan-1,3 dioic acid:- To a solution of sodium ethoxide in absolute ethanol (from sodium, 15.3 g, ethanol 500 ml) was added diethyl malonate (118.7 g). Over a period of 20 minutes and under nitrogen, was then added z,z,z octadeca-6,9,12-trienyl methylsulphonate (120 g). The mixture was heated under reflux for 4 hours. After cooling, the resulting orange gelatinous mass was diluted with a solution of potassium hydroxide (150 g) in water (76 ml) and ethanol (1500 ml), stirred under nitrogen at room temperature for 4 hours and then allowed to stand for 20 hours. The resulting precipitate was filtered off and dissolved in water (2000 ml). The filtrate was evaporated in vacuo and the resultant oil added to the aqueous solution. Acidification (20% aqueous sulphuric acid) with cooling gave an oil which was extracted into diethyl ether (2×1000 ml), the ether layer being washed with water (6×1000 ml). Salt may need to be added to break up emulsions. Drying ($MgSO_4$) and evaporation of the solvent (30° C./20 mmHg and 30° C./0.01 mmHg) gave 2-(z,z,z octadeca-6,9,12-trienyl)propan-1,3-dioic acid(104.5 g, 85%) as an oil which quickly solidified to a yellow low melting solid. This material was used for the next stage.

Stage 3: z,z,z eicosa-8,11,14-trienoic acid:-2-(z,z,z octadeca-6,9,12-trienyl) propan-1,3-dioic acid (104.5 g) was heated under vacuum (140° C./0.01 mmHg) for 5 hours or until the production of carbon dioxide ceased. After cooling, the resulting dark oil was subjected to MPLC (Column size: 65 mm diameter×450 mm, Column packing: Matrex silica, pore size 60A, particle size: 35–70 μm, Solvent: Hexane, Fraction size: 500 ml). Collection of the requisite fractions and removal of the solvent (50° C./20mmHg then 50° C./0.01 mmHg) gave z,z,z eicosa-8,11,14-trienoic acid (68.3 g, 74.5%) as a clear oil.

Secondly, the DGLA is reacted with glycerol with subsequent purification, by the method of stage 6 of Example 1, to give the title tri-DGLA as a clear oil.

Uses

The specified triglycerides have a wide variety of possible uses. They may be used as pharmaceuticals for the treatment or prevention of diseases in which abnormalities of EFAs have been identified. They may be added to foods or be added to or used as nutritional supplements for those who require the particular EFAs for the treatment of prevention of diseases. They may also be used in foods or pharmaceuticals for veterinary use. They may be used for skin Specifically, the triglycerides may be used in the form of an oil for addition to foods or skin care preparations or as a component of a pharmaceutical formulation for oral, topical or parenteral use. The oil used in preparing such foods, skin care products or pharmaceuticals should desirably contain more than 20%, preferably more than 40%, very preferably more than 60% and ideally more than 80% of the particular triglyceride of interest.

The triglycerides may be formulated in any way appropriate, as is well known to those skilled in the art of preparing pharmaceuticals, skin care products or foods. They may be administered orally, enterally, topically, parenterally (subcutaneously, intramuscularly, intravenously or otherwise), rectally, vaginally or by any other appropriate route.

Use Examples

The following are examples of modes of use of the triglycerides;

1. Any one of the specified triglycerides made up in soft or hard gelatin capsules of any size between 100 mg and 1 g and administered to provide a daily dose of between 100 mg and 10 g.
2. Any one of the specified triglycerides microencapsulated in gelatin or agar or any other appropriate material, or incorporated into any appropriate material to form a powder which can be taken orally, added to foods, tabletted, encapsulated, packed in sachets or any other appropriate form.
3. Any one of the specified triglycerides made up in a whip, liquid, cream or other appropriate form for oral administration.
4. Any one of the specified triglycerides made into a cream, ointment or other topical preparation at a concentration ranging from 0.1 to 30%.
5. Any one of the specified triglycerides made up into an emulsion suitable for parenteral administration.
6. Any one of the specified triglycerides added to any appropriate food material such as a spread, drink, candy, cereal, infant food or bakery product.
7. Any of the above may be used in conjunction with oleic acid as such or as its glyceride.
8. As 1 to 7 above, but wherein the glyceride has two residues of the same fatty acid, and one linoleoyl residue.

We claim:

1. A pharmaceutical or dietary composition comprising a triglyceride containing three residues of the same fatty acid selected from the group consisting of a 22:4 n-6 acid, a 22:5 n-6 acid, stearidonic acid, a 20:4 n-3 acid, and a 22:5 n-3 acid in the form of a triple ester with glycerol, wherein said triglyceride forms more than 10% by weight of the triglycerides present.

2. A pharmaceutical or dietary composition comprising a triglyceride containing two residues of the same essential fatty acid (EFA) selected from the group consisting of dihomo-gamma-linolenic acid and the n-6 EFAs naturally derived therefrom and stearidonic acid and the n-3 EFAs naturally derived therefrom, in the form of a 1,2-double ester with glycerol in which the other esterifying acid is a single residue of linoleic acid, wherein said triglyceride forms more than 10% by weight of the triglycerides present.

3. A pharmaceutical or dietary composition comprising a triglyceride containing two residues of the same fatty acid selected from the group consisting of dihomo-gamma-linolenic acid and the n-6 EFAs naturally derived therefrom, stearidonic acid, a 20:4 n-3 acid and a 22:5 n-3 acid, in the form of a 1,3-double ester with glycerol in which the other esterifying acid is a single residue of linoleic acid, wherein said triglyceride forms more than 10% by weight of the triglycerides present.

4. The pharmaceutical or dietary composition of claim 1, 2 or 3 wherein said triglyceride is more than 30% by weight of the triglycerides present.

5. The pharmaceutical or dietary composition of claim 1, 2 or 3 wherein said triglyceride is more than 70% by weight of the triglycerides present.

6. The pharmaceutical or dietary composition of claim 1, 2 or 3 wherein said triglyceride is more than 90% by weight of the triglycerides present.

7. A pharmaceutical composition according to claim 1, 2 or 3 containing a daily dose of 1 mg to 100 g of said triglyceride.

8. A pharmaceutical or dietary composition comprising a triglyceride containing three residues of the 22:6 n-3 acid in the form of a triple ester with glycerol, wherein said triglyceride is more than 40% by weight of the triglycerides present.

9. The pharmaceutical or dietary composition of claim 8 wherein said triglyceride is more than 70% by weight of the triglycerides present.

10. The pharmaceutical or dietary composition of claim 9 wherein said triglyceride is more than 90% by weight of the triglycerides present.

11. A pharmaceutical composition according to claim 8 containing a daily dose of 1 mg to 100 g of said triglyceride.

12. A triglyceride comprising a fatty acid selected from the group consisting of a 22:4 n-6 acid, a 22:5 n-6 acid, a 20:4 n-3 acid, a 22:5 n-3 acid in the form of a triple ester with glycerol.

13. A triglyceride comprising two residues of the same fatty acid selected from the group consisting of dihomo-gamma-linolenic acid and the n-6 EFAs naturally derived therefrom and a 20:4 n-3 acid and a n-3 EFAs naturally derived therefrom in the form of a 1,2-double ester with glycerol in which the other esterifying acid is a single residue of linoleic acid.

14. A triglyceride comprising two residues of the same fatty acid selected from the group consisting of dihomo-gamma-linolenic acid and the n-6 EFAs naturally derived therefrom, a 20:4 n-3 acid and a 22:5 n-3 acid, in the form of a 1,3-double ester with glycerol in which the other esterifying acid is a single residue of linoleic acid.

* * * * *